United States Patent [19]
Gila et al.

[11] Patent Number: 5,846,895
[45] Date of Patent: Dec. 8, 1998

[54] SUPPORTED METALLOCENE COMPLEX AND PROCESS FOR ITS PREPARATION

[75] Inventors: Liliana Gila; Antonio Proto; Evelina Ballato, all of Novara; Diego Vigliarolo; Gabriele Lugli, both of Milan, all of Italy

[73] Assignee: Enichem S.p.A., Milan, Italy

[21] Appl. No.: 837,898

[22] Filed: Apr. 22, 1997

[30] Foreign Application Priority Data

May 15, 1996 [IT] Italy .................................. 000973 96/A

[51] Int. Cl.[6] .............................. C08F 4/02; C08F 4/656; C08F 10/00
[52] U.S. Cl. .......................... 502/107; 502/104; 502/117; 502/120; 526/97; 526/124.6; 526/129; 526/941; 526/156
[58] Field of Search .................................. 502/104, 107, 502/120

[56] References Cited

U.S. PATENT DOCUMENTS

| | | | |
|---|---|---|---|
| 5,071,808 | 12/1991 | Antberg et al. | 526/160 |
| 5,202,398 | 4/1993 | Antberg et al. | 526/129 |
| 5,627,246 | 5/1997 | Langhauer et al. | 502/120 |
| 5,629,255 | 5/1997 | Hafner et al. | 526/160 |
| 5,643,847 | 7/1997 | Walzer | 502/120 |

*Primary Examiner*—Edward J. Smith
*Attorney, Agent, or Firm*—Oblon, Spivak, McClelland, Maier & Neustadt, P.C.

[57] ABSTRACT

A supported metallocene complex of a metal M selected from Ti, Zr or Hf, is prepared by a process comprising, in a first step, the reaction of an inorganic carrier containing hydroxyl groups with a compound (II) containing a cyclopentadienyl group and at least one alkoxysilane group reactive with said hydroxyl groups so as to chemically bind said cyclopentadienyl group to said carrier; and in a second step the reaction with a complex of said metal M capable of reacting with said supported cyclopentadienyl group without carrying out any intermediate metallation of the latter. This process is simple and convenient, and enables high concentrations of metal stably bound to the carrier, to be reached. The complex thus obtained can be used as solid component of a catalyst active in the polymerization of α-olefins, in the presence of a suitable co-catalyst, preferably consisting of an organo-oxygenated derivative of aluminum.

17 Claims, No Drawings

SUPPORTED METALLOCENE COMPLEX AND PROCESS FOR ITS PREPARATION

The present invention relates to a supported metallocene complex and a process for its preparation.

More specifically, the present invention relates to a process for the preparation of a metallocene complex supported on an inert solid, which, in contact with an organo-oxygenated derivative of a non-transition metal, preferably an aluminoxane, is capable of homo-polymerizing or co-polymerizing ethylene and/or α-olefins. The present invention also relates to complexes obtained by said process and the catalysts deriving from these, as well as their use for polymerizing α-olefins.

It is generally known in the art that ethylene, or alpha-olefins in general, can be polymerized by processes at low or medium pressure with catalysts based on a transition metal, generally known as Ziegler-Natta type catalysts. The catalysts which can be used for the purpose generally consist of a compound of at least one transition metal (elements of groups 3 to 10 of the periodic table of elements) mixed with an organometallic compound or hydride of elements of groups 1, 2 or 13 of the periodic table, operating in suspension, in solution, or also without solvents or diluents. For this known technique reference should be made to the description of J. Boor, in "Ziegler-Natta Catalysts and Polymerization", Academic Press, New York (1979).

A particular group of catalysts active in the polymerization of α-olefins consists of the combination of an organic oxyderivative of aluminum (commonly defined as aluminoxane) with an $\eta^5$-cyclopentadienyl derivative of a metal such as titanium, zirconium or hafnium (group 4 of the periodic table), also commonly called metallocene, which can be defined in its most general form with the following formula (I):

(I)

wherein M represents a metal of said group 4, formally in oxidation state +4, and is preferably titanium or zirconium, $R^1$ and $R^2$ each independently represent a group of an anionic nature such as, for example, a hydride, a halide, a phosphonated or sulfonated anion, an alkyl or alkoxy group, an aryl or aryloxy group, an amide group, a silyl group, etc.; Cp independently represents a ligand of the $\eta^5$-cyclopentadienyl type and is generally selected from $\eta^5$-cyclopentadienyl, $\eta^5$-indenyl $\eta^5$-fluorenyl and their derivatives variously substituted; $R^3$, independently of the nature of the other substituents, can have any of the meanings of the ligand Cp, or of groups $R^1$ or $R^2$. "Bridged" metallocenes have also proved to be of particular interest in the known art, wherein two Cp groups, the same or different, are bound by means of a covalent bridge which usually also comprises other carbon atoms or hetero-atoms.

For a known technique for the preparation of the above compounds, reference should be made to the description of H. Sinn, W. Kaminsky, in Adv. Organomet. Chem., vol. 18 (1980), page 99 and to the patent U.S. Pat. No. 4,542,199.

These catalysts have a high catalytic activity, and the capacity to produce polymers with the desired characteristics depending on the particular catalytic composition used and the olefin, or mixture of olefins, subjected to polymerization. See for example, among the numerous documents published on the matter, the description of patents U.S. Pat. Nos. 4,530,914, 4,935,474, 4,937,299 and 5,001,205, and European patent applications having publication number 35.242, 318.049, 384.171 and 387.609.

Particular metallocenes having a structure comprising a single $\eta^5$-cyclopentadienyl ligand and ligands of the alkylamide type ($-NR_2$) are described in European patent application number 476.671.

In spite of the numerous advantages, also catalysts based on metallocenes have several drawbacks, such as, for example, the production of polyolefins in an excessively fine granulometric form. Another problem cited in the known art derives from the low stability of metallocenes, especially titanium, when used as such in polymerization processes at a high pressure (>500 bars) and temperature (about 200° C.). A further disadvantage is the practical impossibility to use metallocenes as such in polymerization processes in gas phase. These processes are always used more frequently in industry as they allow very high yields with a simplified technology for obtaining the polymer from the reactor. Polymerization catalysts based on metallocenes however are generally used in a liquid medium and cannot be handled as such in processes in gas phase.

To resolve, or at least partly, the above disadvantages, a proposal was made to support metallocenes active in polymerization on suitable solid carriers which are able to fix the complex, keeping however the original activity and selectivity substantially unvaried or possibly improving them. Carriers frequently used for the purpose consist of porous inorganic oxides such as silica, alumina and aluminosilicates, or they can be polymeric substrates such as, for example, polystyrene.

The polymerization catalysts thus obtained therefore consist of a solid component comprising the supported metallocene and an organic compound of aluminum, which is normally again an aluminoxane.

Methods for the preparation of these supported metallocenes which comprise the simple contact, usually in a liquid medium, of the porous carrier with the metallocene, are described, for example, in U.S. Pat. No. 5,122,491.

Although some of the disadvantages mentioned above have been at least partly overcome with the supported catalysts thus prepared, numerous problems still remain to be solved for an ideal application of metallocenes in the industrial polymerization of olefins, such as, for example, the fact that at least a part of the supported metallocene can become detached from the support during the polymerization thus acting as homogeneous catalyst which produces a polymer with undesired characteristics. In this way, the final polymerization product can be heterogeneous and with a high content of fine powders. In addition, the activity of these supported metallocene catalysts is still unsatisfactory with respect to the high productivities of analogous homogeneous ones.

The methods for obtaining supported metallocenes active in the polymerization of olefins frequently comprise treatment of the carrier with methylalumoxane before carrying out the contact with the metallocene, as described, for example in European patent applications EP-A 442.725 and EP-A 516.458.

The solid components thus obtained however still do not allow completely satisfactory catalytic activities to be reached, which are comparable to those with analogous metallocenes in homogeneous phase or with respect to the traditional heterogeneous Ziegler-Natta type catalysts. In addition, in these solid components obtained by supporting first the aluminoxane and then the metallocene, it is not possible, in practice, to modify the Al/M ratio during polymerization, with consequent operating limitations of the process.

In another attempt to obtain solid components based on heterogenized metallocenes, a proposal has also been made to carry out a prepolymerization with the formation of a polymeric powder containing the catalyst, followed by the real polymerization, as cited, for example, in patent application EP-A-442.725. Also in these cases, however, the productivity of the catalyst is not completely satisfactory, and a prepolymerization step is required, resulting in further investment and production costs for the industrial embodiment of the process.

In a subsequent approach to the development of catalysts based on supported metallocenes, an attempt was made to chemically bind the $\eta^5$-cyclopentadienyl ligand to the inorganic carrier. For this purpose, for example, published Japanese patent application 5-17515 describes treatment with silica in powder form with dimethyldichlorosilane, followed by reaction with an hydroxyalkylcompound whose molecule contains two cyclopentadienyl rings capable of subsequently forming a metallocene complex with an atom of titanium or zirconium. There is no proof however of the formation of the above metallocene chemically bound to the inorganic carrier, and in addition, the method proposed for carrying out the supporting seems particularly complex and difficult without providing any particular advantages with respect to other supported metallocenes of the known art. In fact, the normal method for the formation of the metallocene complex, i.e. the reaction of a preformed cyclopentadienyl anion starting from the desired ligand, with a halide of a transition metal, does not give a satisfactory yield and selectivity when said cyclopentadienyl ligand is already supported.

U.S. Pat. No. 5,202,398 describes a supported metallocene obtained by reacting an inorganic oxide with a metallocene having a cyclopentadienyl, ring functionalized with an alkoxysilane group. Also in this case, however, the method described requires the preliminary preparation of specific functionalized metallocenes which do not have satisfactory versatility in relation to the various industrial demands of polyolefins. In fact, the preparation of intermediate metallocene complexes having a branched alkoxysilane group, is particularly difficult. In addition, this method does not give satisfactory yields with respect to the quantity of complex used initially, with considerable reduction in the economy of the process.

There therefore still remains a great demand for improving the characteristics of supported metallocenes suitable for the polymerization of olefins, which overcome the various drawbacks discussed above.

The Applicant has now found a simple and convenient process for the preparation of supported metallocene complexes, which are capable of polymerizing α-olefins in the presence of an organo-oxygenated compound of aluminum or other metals of groups 13 and 14 of the periodic table.

This method lacks many of the disadvantages mentioned above and enables supported catalysts to be obtained with a high purity and high content of transition metal.

In particular, it has been found that it is possible to support compounds having a metallocene structure on inorganic oxides, by means of a simple and effective process comprising anchoring a functionalized cyclopentadienyl ring on the surface of said oxides, followed by the reaction with a particular group of compounds of the transition metal.

It has also been found that these supported metallocenes, as well as being obtained with a simple process which is easy to effect, are relatively stable and can be used as catalysts with a high activity in the polymerization of olefins when combined with an aluminoxane.

A first object of the present invention therefore relates to a process for the preparation of a metallocene complex of titanium, zirconium or hafnium, supported on an inorganic solid, comprising the following steps in succession:

(a) putting in contact and reacting, preferably in an inert liquid medium, said inorganic solid, having hydroxide groups on the surface, which are reactive with an alkoxysilane group, with at least one organic compound having the following formula (II):

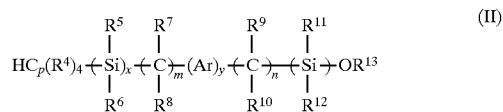

wherein:

$C_p$ represents a cyclopentadienyl ring; each $R^4$ can independently be hydrogen, halogen, a $C_1$–$C_8$ alkyl group, a $C_3$–$C_{12}$ alkylsilyl group, a $C_5$–$C_8$ cycloalkyl group, a $C_6$–$C_{14}$ aryl group, a $C_6$–$C_{15}$ arylalkyl group, a $C_1$–$C_8$ alkoxy group, a $C_1$–$C_8$ alkylcarbonyloxy group, or two adjacent $R^4$ groups can combine with each other to form an aliphatic or aromatic cyclic structure comprising in the cycle at least three, and preferably from 5 to 8 non-metal atoms different from hydrogen and halogen;

$R^5$ and $R^6$ can, independently of each other, be a $C_1$–$C_5$ alkyl group, a $C_5$–$C_8$ cycloalkyl group, a $C_6$–$C_{12}$ aryl group, a $C_7$–$C_{12}$ arylalkyl group or a $C_1$–$C_5$ alkoxy group, and are preferably selected from methyl or ethyl;

$R^7$, $R^8$, $R^9$ and $R^{10}$ can, independently of each other, be hydrogen, a $C_1$–$C_5$ alkyl group, a $C_5$–$C_8$ cycloalkyl group, a $C_6$–$C_{12}$ aryl group, a $C_7$–$C_{12}$ arylalkyl group or a $C_1$–$C_5$ alkoxy group, and are preferably hydrogen or methyl;

$R^{11}$ and $R^{12}$ can, independently of each other, be a $C_1$–$C_5$ alkyl group, a $C_5$–$C_8$ cycloalkyl group, a $C_6$–$C_{12}$ aryl group, a $C_7$–$C_{12}$ arylalkyl group or a $C_1$–$C_5$ alkoxy group, and are preferably methyl;

$R^{13}$ is a $C_1$–$C_5$ alkyl group, preferably methyl or ethyl;

Ar is an divalent aromatic or heteroaromatic $C_3$–$C_{16}$ group, preferably ortho-,para-, or meta-phenylene. the indexes "m" and "n" can be 0, in which case the indexed group is absent, or can independently have all the integer values between 1 and 4, the indexes "x" and "y" can independently have the value of 0 or 1, depending on whether the indexed group is present or absent, to obtain an inorganic solid functionalized with cyclopentadienyl groups;

(b) putting in contact and reacting, in an inert liquid medium, said functionalized inorganic compound with a compound of a metal M having the following formula (III):

wherein:

M represents a metal selected from titanium, zirconium or hafnium;

R' and R" each independently represent a substituent group selected from a hydrogen or halogen atom, a $C_1$–$C_8$ alkyl group, a $C_3$–$C_{12}$ akylsilyl group, a $C_5$–$C_8$ cycloalkyl group, a $C_6$–$C_{10}$ aryl group, a $C_1$–$C_8$ alkoxy group, a $C_2$–$C_{10}$ dialkylamide group and a $C_4$–$C_{20}$ alkylsilylamide group;

R''' represents a substituent group of the same nature as the previous groups R' and R", selected independently of these, or an anion containing an $\eta^5$-cyclopentadienyl ring co-ordinated to the metal M; and B represents a $C_1$–$C_8$ alkyl group, a $C_5$–$C_8$ cycloalkyl group, a $C_6$–$C_{10}$ aryl group or a $C_2$–$C_{10}$ dialkylamide group;

to form said supported metallocene complex.

The inorganic solid which can be used as carrier according to the process of the present invention can be selected from various inorganic solid materials characterized by the presence of hydroxide——OH groups on their surface. These inorganic solids are preferably porous materials having a high surface development per volume unit. Typical inorganic solids suitable for the purpose are oxides, carbonates, phosphates, silicates. Typical examples of oxides are porous oxides of a metal M' selected from silicon, aluminum, titanium, zirconium, calcium, barium, zinc, magnesium or a mixture of these metals, preferably in granular or powder form.

The inorganic solids suitable for the present invention are preferably porous oxides having an average particle size of between 0.1 and 500$\mu$, preferably between 5 and 200$\mu$, a pore volume of between 1 and 3 ml/g and an available surface of between 50 and 400 m$^2$/g, preferably between 100 and 300 m$^2$/g. They are characterized by the presence of M'—OH groups on the surface in concentrations normally of between 0.1 and 2.0 mmoles/g, preferably between 0.4 and 1.0 mmoles/g.

Porous oxides which can be used in step (a) of the present process are preferably silica, alumina or aluminosilicates. These are all commercially available with the particle size, surface extension and pore volume characteristics listed above. Particularly preferred for the purposes of the present invention is silica, such as, for example, that sold under the trade-names of "GRACE 948" and "CROSSFIELD HP39".

Before being used in the process of the present invention, the silica, as all the other porous oxides mentioned above, is preferably subjected to drying to eliminate most of the water possibly adsorbed on the surface. This drying can be carried out, for example, at temperatures of between 150° and 800° C., under vacuum or in a stream of nitrogen or dry air, for times normally between 1 and 5 hours. The drying process also determines the concentration of —OH groups on the surface, which can therefore be adjusted, by modifying the time and drying temperature, to the desired value, within the range specified above.

The silylorganic compound having the above formula (II) is characterized in that it has an alkoxysilane group at one end and a cyclopentadienyl group at the other which can be variously substituted. The alkoxysilane group is capable of reacting with the hydroxyl groups of the above inorganic solid forming a covalent bond of the type Si——O——M' which binds in a relatively stable way the organic compound having formula (II) to the surface of the solid. The cyclopentadienyl group ——HC$_p$(R$^4$)$_4$ is preferably a cyclopentadiene (——C$_5$H$_5$), indene or fluorene group, or a derivative of one of the above groups, in which one or more carbon atoms of the molecular skeleton (included or not included in the cyclopentadienyl ring), are substituted with $C_1$–$C_5$ alkyl or alkylsyl groups, or $C_6$–$C_{10}$ aryl or aryalkyl groups, or $C_1$–$C_8$ alkoxy groups. Particularly preferred ——HC$_p$(R$^4$)$_4$ groups are cyclopentadienyl (C$_5$H$_5$), indenyl (C$_9$H$_7$), 4,5,6,7-tetrahydroindenyl (C$_9$H$_{11}$), and their (poly) methylsubstituted derivatives.

According to a preferred aspect of the present invention, in the compound having formula (II), the indexes "m", "x" and "y" are all 0, and "n" is zero, or an integer between 1 and 4. Even more preferably, "m", "n", "x" and "y" are 0, and said compound having formula (II) consists of a ——HC$_p$(R$^4$)$_4$ cyclpentadienyl group possibly substituted, bound to the alkoxysilane group.

The compounds having formula (II) are generally known and some are available commercially. They can be obtained with the normal synthetic methods of organic chemistry at the disposal of the average expert in the field. For example, they can be prepared by the coupling of an alkoxydialkylsilyl chloride having the desired structure with a sodium salt of a cyclopentadienyl group, by mixing and reacting the two compounds at a temperature of less than room temperature, preferably between –20° and 0° C., operating in solution of an inert solvent (preferably an aromatic hydrocarbon or an ether, or one of their mixtures). Typical non-limiting examples of compounds having formula (II) suitable for the purposes of the present invention are indicated below, together with reference to the method for their preparation.

| | |
|---|---|
| MeOSi(Me)$_2$Ind | Starting from MeOSi(Me)$_2$Cl + NaInd according to the process specified above |
| MeOSi(Me)$_2$Cp | "Journal of the American Chemical Society, vol. 90 (1968), pages 4701–4705" |
| EtOSi(Me)$_2$Cp | "Journal of Organometallic Chemistry, vol. 125 (1967), pages 57–62" |
| BuOSi(Me)$_2$CH$_2$Cp | "Makromolekulare Chemi, vol. 104 (1967), pages 67–89" |
| (MeO)$_3$Si(CH$_2$)$_3$Cp | "Journal of Organometallic Chemistry, vol. 315 (1986), pages 143–156" |
| (EtO)$_3$SiCp | "Journal of Organometallic Chemistry, vol. 148 (1978), pages 73–80" |
| BuOSi(Me)$_2$Ind | "Journal of the American Chemical Society, vol. 73 (1951), pages 5135–5138" |
| (BuO)$_2$Si(Me)Ind | Same reference as BuOSi(Me)$_2$Ind |
| (EtO)$_3$Si(CH$_2$)$_3$Cp | Commercial product |

In the above formulae, the following abbreviations are used: Me=methyl, Et=ethyl, Ind=indenyl (C$_9$H$_7$), Bu=butyl, Cp=cyclopentadienyl (C$_5$H$_5$).

Step (a) of the present process can be conveniently carried out by putting the compound having formula (II) in contact with said inorganic solid, and making them react at a temperature of between 50° and 300° C., preferably between 180° and 250° C., for a time which is sufficient to deposit the desired quantity of compound on the inorganic solid. The treatment times vary in relation to the type of inorganic solid, the temperature and concentration of the reagents. The reaction process can be followed by successive sampling and determination of the residual concentration of —OH groups on the surface of the solid, for example by infra-red spectroscopy as described by J. B. Peri in the publication "The Journal of Physical Chemistry, vol. 70(1966), page 2942 onwards. The time is normally sufficient for the characteristic peak at 3750 nm to disappear, usually between 1 and 10 hours.

It is convenient to carry out step (a) in the presence of a suitable inert liquid medium, such as an aliphatic or aromatic hydrocarbon, which has a boiling point higher than or equal to the temperature at which the reaction is to be carried out.

The relative quantities of inorganic solid and compound having formula (II) are preferably such that the molar ratio between the latter and the hydroxide groups present on the surface is higher than the stoichiometric value, more preferably between 1 and 5. However it is obviously up to the expert in the field and within the scope of the present invention to carry out the reaction with a ratio of less than 1, when a lower concentration of compound having formula (II) bound on the surface of the inorganic solid is required.

During step (a), the —OH group on the surface of the inorganic solid reacts with at least one alkoxide group (for example —$OR^{13}$) bound to the silicon atom in the compound having formula (II), with the formation of the corresponding $R^{13}$—OH alcohol and a covalent bond between the inorganic solid and said silicon atom. At the end of step (a), the average molar quantity of compounds having formula (II) thus supported on said inorganic solid is preferably between 90 and 100% of the hydroxide groups present on the surface available before the reaction.

Step (b) of the present process comprises the formation of the metallocene supported on said inorganic solid by reacting the $C_p$ groups of the compound having formula (II) supported according to step (a), with a compound of the metal M having the previous formula (III).

The metal M is preferably Ti or Zr.

In formula (III) the R' and R" groups can each independently represent a hydrogen atom or a halogen atom, such as chlorine or bromine, a $C_1$–$C_8$ alkyl group such as, for example, methyl, ethyl, butyl, isopropyl, isoamyl, octyl, benzyl, a $C_3$–$C_{12}$ alkylsilyl group such as, for example, trimethylsilyl, triethylsilyl or tributylsilyl, a cycloalkyl group such as cyclopentyl or cyclohexyl, a $C_6$–$C_{10}$ aryl group such as phenyl or toluyl, a $C_1$–$C_8$ alkoxy group such as, for example, methoxy, ethoxy, iso- or sec-butoxy, or a $C_2$–$C_{10}$ dialkylamide or $C_4$–$C_{20}$ alkylsilylamide group, preferably of the type represented by the general formula —$NR^{14}R^{15}$ wherein $R^{14}$ and $R^{15}$ are alkyl groups having from 1 to 4 carbon atoms, such as, for example, methyl, ethyl or butyl groups, or, in the case of alkylsilylamides, alkylsilyl groups having from 3 to 6 carbon atoms such as, for example, trimethylsilyl or triethylsilyl.

The groups R' and R" having formula (III) preferably represent an alkyl, alkoxyl or dialkylamide —$NR^{14}R^{15}$ group, the latter being particularly preferred.

According to the present invention, R'" in formula (III) can have any of the meanings previously defined for groups R' and R", or can be a group containing an $\eta^5$-cyclopentadienyl ring, co-ordinated to the metal M. R'" preferably represents a dialkylamide group or an anion containing an $\eta^5$-cyclopentadienyl ring which preferably derives (formally by extraction of an $H^+$ ion) from a molecule of cyclopentadiene, indene or fluorene, or from a derivative of one of the above compounds, in which one or more carbon atoms of the molecular skeleton (included,or not included in the cyclopentadienyl ring) are substituted with $C_1$–$C_8$ alkyl or silylalkyl groups, or $C_6$–$C_{10}$ aryl or aryloxy groups, or $C_1$–$C_8$ alkoxy groups.

In a preferred embodiment of the process of the present invention, the groups R', R" and R'" of the compound having formula (III) used in step (c), all represent —$NR^{14}R^{15}$ dialkylamide groups, preferably the same, such as for example dimethylamide or diethylamide.

In a second preferred embodiment of the present invention, R' and R" are again dimethylamide or diethylamide groups, and R'" is a second $\eta^5$-cyclopentadienyl group co-ordinated to the metal M, having, for example, the structure of cyclpentadienyl ($C_5H_5$), indenyl ($C_9H_7$) or a (poly)methylsubstituted derivative of these. In a particular form, R'" can have the same structure as the group $C_p(R^4)_4$ in the compound having formula (II), in which, however, the bond with the remaining part of the molecule is substituted with a further $R^4$ group.

Groups B in formula (III), suitable for the purposes of the present invention, are, for example, $C_1$–$C_8$ alkyl groups such as methyl, ethyl, butyl, isopropyl, isoamyl, octyl, benzyl, cycloalkyl groups such as cyclopentyl or cyclohexyl, or $C_2$–$C_{14}$ dialkylamide groups, preferably of the type which can be represented with the above general formula —$NR^{14}R^{15}$ wherein $R^{14}$ and $R^{15}$ are alkyl groups having from 1 to 4 carbon atoms, such as, for example, methyl, ethyl or butyl groups. Preferred B groups are dialkylamide groups, particularly dimethylamide and diethylamide.

Preferred specific compounds having formula (III) for the purposes of the present invention are, f. ex.: $Zr(NEt_2)_4$; $(\eta^5\text{-}C_5H_5)Zr(NEt_2)_3$; $Zr(NMe_2)_4$; $(\eta^5\text{-}C_5H_5)Ti(NMe_2)_3$; $Zr(NMe_2)_4$; $(\eta^5\text{-Ind})ZrCl_2(NEt_2)$; $HfCl_3(NEt_2)$; $ZrCl_3(NEt_2)$; $(\eta^5\text{-}C_5H_5)TiCl_2(NMe_2)$; $(\eta^5\text{-}C_5H_5)TiMe_3$; $(\eta^5\text{-Ind})ZrBz_3$.

In the above formulae, the abbreviations have the same meaning previously defined for the specific compounds having formula (II).

The compounds included in formula (III) are generally known and can however be easily prepared with one of the known methods in organometallic chemistry described for example in "Comprehensive Organometallic Chemistry" G. Wilkinson et al. Editors, vol. 3(1982), pages 298–615. Many of the amide derivatives included in formula (III) can be prepared as indicated by G. Chandra et al. in the publication "J. of Chemical Soc.", sect. A, (1968), pages 1940–1945. Other methods for the preparation of amidoderivatives having formula (III) are described in European patent application EP 476.671. The contents of these publications are included in the present description as reference.

According to the present invention, step (b) can be conveniently carried out in a liquid medium consisting of a hydrocarbon solvent, preferably aromatic, leaving the functionalized porous inorganic solid in contact with the cyclopentadienyl groups (obtained according to step (a)) and the compound having formula (III), at a temperature of between 70° and 150° C., preferably between 90° and 130° C., and for a period preferably of between 4 and 12 hours. Particularly aromatic solvents are toluene or xylenes.

The ratios between the reagents, which can be used in step (b) of the present process, are determined in relation to the desired concentration of metallocene on the carrier. The selection of these ratios is up to the expert in the field, using the compound having formula (III) in excess with respect to the molar quantity of the groups having formula (II) on the carrier if the latter are to be completely reacted, whereas compound (III) will be used in defect if the final concentration of supported metallocene is to be kept at a lower level. The formation reaction of the supported metallocene is generally quantitative. A strong excess of compound having formula (III) is not advisable however to avoid undesired adsorption phenomena.

The molar ratio between the groups having formula (II) on the carrier and the compound having formula (III) is preferably between 0.5 and 2.0, particularly between 1.0 and 1.2.

According to the process of the present invention, it is not necessary to effect a preliminary metallation of the —$HC_p(R^4)_4$ group on the carrier, before carrying out the reaction with the compound having formula (III), as described in published Japanese patent application 517515 previously mentioned. On the contrary, during the preliminary experimentation carried out by the Applicant, it was observed that this metallation, if effected, does not enable the production of supported metallocenes having all the desired properties of those of the present invention. This preliminary metallation in fact is thought to cause a loss in a considerable quantity of compounds having formula (II) covalently bound to the carrier, with a consequent reduction in the potential activity of the solid catalyst component.

Without any intention of limiting the scope of the present invention to any particular theory, it is thought that group B having formula (II) should have a basic character (when considered in its anionic form) which is at least sufficient to extract, under the operating conditions of step (b), a hydrogen ion from group $C_p$ bound to the surface of the porous oxide. The alkyl, cycloalkyl, aryl and particularly amide groups represented by group B.

The supported metallocene complex obtained as above can be subsequently isolated by removal of the liquid medium, preferably by decanting or filtering, or it can be used as such in suspension in the same liquid medium. An effective washing of the supported metallocene, for example with a solvent in which the compound having formula (III) is soluble, is usually advisable when it is necessary to avoid ensuing interference in the polymerization process on the part of these compounds possibly adsorbed on the surface of the carrier, without being co-ordinated to the cyclopentadienyl group having formula (II). The adsorbed compounds can in fact be freed in the polymerization mixture giving rise to the formation of polymers with a structure, molecular weight and morphology different from those desired. Operating as described above, a supported complex is obtained, according to the present invention, which does not release significant quantities of compounds of the metal M, even by means of extraction with a solvent at reflux.

The process of the present invention enables both mono- and bis-cyclopentadienyl supported complexes to be easily obtained with the same synthetic method. In particular, the latter are characterized by the presence of a cyclopentadienyl group bound to the inorganic carrier, and a cyclopentadienyl group bound only to the metal M. These asymmetrical complexes cannot be easily obtained with simple methods and high yields using the processes of the known art, especially in the case of complexes with cumbersome ligands such as bis-indenyls which however are particularly active and have interesting aspects linked to the freedom of movement of the molecule.

A second object of the present invention relates to a metallocene complex supported on an inorganic solid, preferably consisting of a porous oxide of a metal M' as previously defined, said supported metallocene having the following formula (IV):

wherein:
M represents a metal selected from titanium, zirconium or hafnium;
A is an anion containing an $\eta^5$-cyclopentadienyl ring co-ordinated to the metal M,
R' and R" each independently represent a substituent group selected from a hydrogen or halogen atom, a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxy group, a $C_2$–$C_{10}$ dialkylamide group and a $C_4$–$C_{20}$ alkylsilylamide group;
R'" represents a substituent group of the same nature as the previous groups R' and R", selected independently of these, or a second anion containing an $\eta^5$-cyclopentadienyl ring co-ordinated to the metal M;
characterized in that at least one, preferably at least two, of the above R', R" or R'" is selected in the group of substituents consisting of: the $C_1$–$C_8$ alkyl groups, the $C_5$–$C_8$ cycloalkyl groups, the $C_2$–$C_{10}$ dialkylamide groups, and said $\eta^5$-cyclopentadienyl anion A is formally derived from said functionalized inorganic solid obtained according to the above step (a) of the process of the present invention, by extraction of a hydrogen ion ($H^+$) from the —$HC_{p(R}{}^4)_4$ group in the compound having formula (II).

This $\eta^5$-cyclopentadienyl anion A can be represented by the following formula (V),

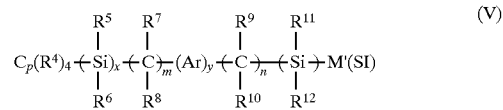

wherein:
$C_p$ represents an $\eta^5$-cyclopentadienyl ring of an anionic nature, co-ordinated to said metal M;
M'(SI) represents said inorganic solid comprising the metal M' preferably one of its porous oxides, bound with a covalent bond to the complex of the metal M;
the symbols $R^4$, $R^5$, $R^6$, $R^7$, $R^8$, $R^9$, $R^{10}$, $R^{11}$, $R^{12}$, Ar, "m", "n", "x" and "y" have the same general or particular meaning previously specified for the compounds having formula (II).

The above supported metallocene complex can be conveniently prepared by the above process in accordance with the present invention.

In a preferred embodiment of the present invention, the groups R', R" and R'" having formula (IV) all represent —$NR^{14}R^{15}$ dialkylamide groups, more preferably the same, such as for example dimethylamide or diethylamide.

In a second preferred embodiment of the present invention, R' and R" are again dialkylamide groups as previously defined, R'" is a second $\eta^5$-cyclopentadienyl group co-ordinated to the metal M, which, analogously to A, derives from a molecule of cyclopentadiene, indene or fluorene, or from one of the corresponding derivatives substituted on the rings. This second $\eta^5$-cyclopentadienyl group is not however directly bound to the porous carrier consisting of the oxide of the metal M'. Particularly preferred, in the latter case, are the metallocenes having formula (IV) wherein R' and R" are dimethylamide or diethylamide and R'" is cyclopentadienyl ($C_5H_5$), indenyl ($C_9H_7$), tetrahydroindenyl ($C_9H_{11}$), or a (poly) methylsubstituted derivative of these.

Also included in the scope of the present invention are those solid catalyst components in which two or more complexes having formula (IV) mixed each other, are present, bound to the porous inorganic carrier.

The supported metallocene complex of titanium, zirconium or hafnium which can be obtained with the process of the present invention and particularly having the above formula (IV), can form a solid component of catalyst capable of (co)polymerizing α-olefins, combined with a suitable co-catalyst, preferably consisting of an oxygenated alkyl derivative of aluminum, gallium or tin, more preferably an aluminoxane. Said solid component and co-catalyst therefore form a catalyst for the (co)polymerization of α-olefins.

According to the present invention, an organo-oxygenated derivative of aluminum which is normally an aluminoxane, is preferably used as co-catalyst. As is known, aluminoxanes are compounds containing Al—O—Al bonds, with a varying O/Al ratio, which can be obtained in the art by reaction, under controlled conditions, of an aluminum alkyl, or halide of aluminum alkyl, with water or other compounds containing controlled quantities of available water, such as, for example in the case of aluminum trimethyl, with a salt hydrate, such as aluminum sulfate hexahydrate, copper sulfate pentahydrate and iron sulfate pentahydrate. The aluminoxanes preferably used for the formation of the polymerization catalyst of the present invention are oligo- or polymeric compounds, cyclic or linear, characterized by the presence of repetitive units having the formula:

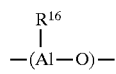

wherein $R^{16}$ is a $C_1$–$C_4$ alkyl group, preferably methyl or ethyl.

Each aluminoxane molecule preferably contains from 4 to 70 repetitive units which may not necessarily be all equal, but contain different $R^6$ groups.

In particular, in the polymerization catalysts of α-olefins of the present invention, the aluminoxane and the solid component are used in such proportions that the atomic ratio between the aluminum in the aluminoxane and the metal M in formula (I) is within the range of 10 to 10000 and preferably from 100 to 5000.

The catalysts of the present invention can be used in the polymerization of ethylene to give linear polyethylene and in the polymerization of propylene or higher alpha-olefins to give atactic, syndiotactic or isotactic polymers depending on the type of supported metallocene or the type of alpha-olefin polymerized. These catalysts are also active in the copolymerization of ethylene with propylene and/or other olefins to obtain in particular LLDPE, VLDPE and ULDPE, with a low content of alpha olefin, and rubbers of the EPR type with a high content of alpha olefin. They can also be used for the terpolymerization of ethylene, propylene and a diene to obtain vulcanized rubbers of the EPDM type.

The catalysts of the present invention can be used with excellent results in substantially all known polymerization processes, such as, for example, processes in suspension, at low, medium or high pressure and at temperatures of between 50° and 240° C.; processes in solution in an inert diluent operating at pressures of from 10 to 150 bars and temperatures of between 120° and 230° C.; or in gas phase, with temperatures generally within the range of 60° to 160° C., at pressures of between 5 and 50 bars. Hydrogen is generally used as molecular weight regulator. In all cases, the catalysts of the present invention are characterized by a high stability and activity, allowing the production of polyolefins with a high molecular weight, with controlled particle size and without fine powders.

The present invention is illustrated in detail by the following examples which however are purely indicative and do not limit the overall scope of the present invention.

The inorganic oxide, used as carrier in the examples, consists of a commercial silica of the type "Grace 948" having an average particle size of 55μ which, unless otherwise indicated, has been preliminarily treated for 5 hours at 800° C. under vacuum, and subsequently manipulated in an inert nitrogen atmosphere. The silica thus treated has a residual content of —OH hydroxide groups of 0.48 mmoles/g.

The quantity of supported transition metal is determined by X-ray fluorescence, using a sequential spectrometer model Philips PW 1404/10. The determination was carried out in accordance with the method described by M. Thomson and J. M. Walsh in the publication "A Handbook of Inductively Coupled Plasma Spectrometry" Ed. Blackie (Glasgow and London), page 105, whose content is included in the present application as reference.

EXAMPLE 1

Preparation of the Supported Complex [(Silica)-O—Si(Me)$_2$Ind]Zr(NEt$_2$)$_3$ (I) Preparation of 1-(methoxydimethylsilyl)indene [IndSi(Me)$_2$(OCH$_3$)]

A solution of sodium indenyl obtained by heating at reflux for 10 hours 16 g of metallic sodium with 49.5 g of indene (0.426 moles) in tetrahydrofuran (THF), is added dropwise, after separation of the excess sodium, to a solution of dimethyl-methoxy-chloro-silane (44.27 g; 0.355 moles) in 150 ml of THF, maintained at −18° C. At the end of the addition the suspension is left to return to room temperature and is heated at reflux for 3 hours. The sodium salt formed is filtered, the filtrate is evaporated and distilled under vacuum at 0.1 mm/Hg collecting the fraction at 60°–64° C. 42 ml of a colourless oily liquid (93.5% purity, determined by mass gaschromatography-spectrometry, GC-MS) are obtained, which on subsequent distillation give 35 ml (38.5 g) of product corresponding to 1-(methoxydimethylsilyl) ndene desired with a purity of 96% (by GC), and a yield of 53% with respect to the starting silane.

(II) Supporting of 1-(methoxydimethylsilyl)indene on silica

A suspension is prepared of 8.3 g of "Grace-948" silica ([OH]=0.48 mmol/g) in 160 ml of methylnaphthaline (distilled under vacuum and conserved on molecular sieves) and is kept under light mechanical stirring. To this, 5 ml of IndSi(Me)$_2$(OCH$_3$) prepared as described above, are added, in a period of about 30 minutes. At the end of the addition, the mixture is heated to reflux (230° C.) for 5 hours, filtered, the solid washed with toluene, then with heptane, then with pentane and dried under vacuum, thus obtaining 8.2 g of indenyl ligand supported on silica [(silica)-O—Si(Me)$_2$Ind], which, upon IR spectroscopy, proved to no longer have any hydroxide group on the surface, and therefore a concentration of supported indenyl groups was indirectly calculated as being approximately equal to that of the initial hydroxide groups, [Ind]=0.48 mmol/g.

(III) Preparation of the Supported Complex 1 ml (2.6 mmoles) of Zr(NEt$_2$)$_4$ are added to a suspension of 3.13 g of (silica)-O—Si(Me)$_2$Ind prepared as described in the previous point (II) (Indenyl=1.5 mmoles) in 60 ml of toluene, maintained under light mechanical stirring. The mixture is filtered under nitrogen, washed with toluene and then with pentane, and dried at the pump. At the end 3.04 g of a cream-coloured solid are obtained, containing zirconium with a concentration [Zr]=0.87% by weight. This concentration does not vary significantly after extraction at reflux with toluene for 24 hours.

EXAMPLE 2

Preparation of the Supported Complex [(Silica)-O—Si(Me)$_2$Ind]Ti(NMe$_2$)$_3$

The synthesis procedure of point (III) of Example 1 was repeated, but using in this case 1.6 g of (silica)-O—Si(Me)$_2$)Ind prepared as described in point (II) (Indenyl=0.78 mmoles), and 440 mg (2 mmoles) of Ti(NMe$_2$)$_4$ instead of the corresponding zirconium salt. At the end 1.5 q of a cream-coloured solid, corresponding to the desired supported complex were obtained, containing 0.57% by weight of Ti. This concentration does not vary after extraction with toluene at reflux for 24 hours.

EXAMPLE 3

Preparation of the Supported Complex [(Silica)-O—Si(Me)$_2$Ind]IndTi(NMe$_2$)$_2$ The synthesis procedure of point (III) of Example 1 was repeated, but using in this case 0.6 g of (silica)-O—Si(Me)$_2$)Ind prepared as described in point (II) (Indenyl=0.30 mmoles), and 200 mg (0.67 mmoles) of IndTi(NMe$_2$)$_3$ instead of the corresponding zirconium salt. At the end 0.55 g of a solid, corresponding to the desired supported complex were obtained, containing 1.17% by weight of Ti. This concentration does not vary after extraction with toluene at reflux for 24 hours.

EXAMPLE 4 (comparative)

Preparation of the Supported Complex (Silica)/ IndTi(NMe$_2$)$_3$ 560 mg of Grace 948 silica treated at 500° C. for 4 h under vacuum [OH]=0.82 mmol/g) and 27 mg (0.09 mmol) of IndTi(NMe$_2$)$_3$ dissolved in 50 ml of toluene are charged, at room temperature, into a 100 ml glass test-tube equipped with a propeller stirrer. The mixture is left under stirring at 70° C. for two hours, is then filtered, washed three times with toluene and then with pentane and dried under vacuum. A solid containing 0.32% by weight of Ti is obtained.

EXAMPLE 5

Preparation of the Supported Complex [(Silica)- O—Si(CH$_3$)$_2$Cp]CpZr(NMe$_2$)$_2$ (I) Synthesis of Methoxydimethylsilylcyclopentadiene [CpSi(Me)$_2$(OCH$_3$)]

16.8 ml (0.22 moles) of a suspension of sodium in toluene at 30% are charged into a 250 ml flask. The mixture is diluted with 100 ml of THF and cooled to 0° C. 18.5 ml (0.22 moles) of cyclopentadiene diluted in 50 ml of THF are slowly added dropwise (about 60 minutes). The resulting solution is left under stirring at room temperature for a whole night, is then cooled to 0° C. and 29 ml (0.22 moles) of methoxydimethylchlorosilane fresh distillate (PETRARCH: 90%) are slowly added dropwise. The reaction is carried out at 0° C. for 3 hours. After filtration of the salt formed and evaporation of the solvent, a dark yellow oily liquid is obtained which, on distillation at 160°–162° C. gives 7.5 g of the desired product with a purity of 95.5% (GC), and a yield of 24%.

(II) Preparation of Methoxydimethylsilylcyclopentadiene Supported on Silica.

With the same procedure described under point (II) of example 1, but using 3.0 ml of CpSi(Me)$_2$(OCH$_3$) instead of IndSi(Me)$_2$(OCH$_3$), and 8.4 g of "Grace 948" silica having [OH]=0.58, a supported cyclopentadiene ligand, herein indicated with the formula (silica)-O—Si(Me$_2$)Cp, is prepared, having a concentration of 0.58 mmol/g of bound cyclopentadiene groups, calculated as described above.

(III) Preparation of the Supported Complex 2.25 g of the supported ligand (silica)-O—Si(Me$_2$)Cp prepared as above (cyclopentadienyl=1.305 mmoles), were treated with 0.84 g (29 mmoles) of CpZr(NMe$_2$)$_2$ according to the procedure described under point (III) of Example 1, obtaining 2.15 g of a yellow solid, corresponding to the desired supported complex, containing 1.99% by weight of Zr. This concentration does not vary after extraction with toluene at reflux for 24 hours.

EXAMPLE 6(comparative)

Preparation of Supported Complex (Silica)-O—Si (CH$_2$)$_2$Cp$_2$ZrCl$_2$

For comparative purposes, the preparation of the supported complex (Silica)-O—Si(CH$_2$)$_2$Cp$_2$ZrCl$_2$ is repeated using the procedure described in patent U.S. Pat. No. 5,202,398 (Antberg M. et al., at the company Hoechst). In accordance with this procedure, a silica suitably treated to have the desired concentration of surface —OH groups, is reacted with the complex H$_3$C—O—Si(CH$_2$)$_2$Cp$_2$ZrCl$_2$, previously prepared.

(I) Synthesis of (methoxydimethylsilylcyclopentadienyl) cyclopentadienylzirconium dichloride [H$_3$C—O—Si(CH$_2$) $_2$Cp$_2$ZrCl$_2$]

3.73 ml (48 mmoles) of a suspension of sodium at 30% in toluene are diluted with 130 ml of dimethoxyethane (DME), cooled to 0° C. and to which a solution has been added, prepared by dissolving 7.5 g (48 mmoles) of the ligand CpSi(Me)$_2$(OCH$_3$), prepared as described under point (I) of example 5, in 20 ml of DME. The mixture is left under stirring for the whole night at room temperature; the solvent is evaporated and the residue is resuspended in 40 ml of THF. This is then slowly added dropwise to a solution of CpZrCl$_2$.2THF (19.6 g; 48 mmoles) in 150 ml of THF maintained at −50° C. The mixture is left under stirring at −20° C. for 2 hours and subsequently at room temperature for a night. The salt formed is filtered, the solvent is evaporated and the residue washed several times with pentane.

3.5 g of a solid white product are obtained which, upon $^1$H NMR analysis, proves to be a mixture of the desired complex H$_3$C—O—Si(CH$_2$)$_2$Cp$_2$ZrCl$_2$ with about 30% of a coproduct, having a structure difficult to identify but which however does not contain alkoxide (methoxide) groups reactive with the silica.

$^1$H NMR (CDC$_3$): 0.41 ppm (6H, s); 3.44 ppm (3H,s); 6.49 ppm (5H, s); 6.55 ppm (2H, m); 6.79 ppm (2H, m).

(II) Preparation of the Supported Complex 2.76 g of "Grace 948" silica treated for 4 hours under vacuum at 500° C. ([OH]=2 mmoles) are suspended in 20 ml of toluene, cooled to 0° C. and to which a solution has been added obtained by dissolving 445 mg (1.0 mmoles of zirconium) of the product obtained according to the previous point (I) in 10 ml of toluene. The reaction is carried out at room temperature for 15 hours. The solid is then filtered, washed three times with ether and finally dried under vacuum at room temperature for 8 hours. 2.28 g of a solid are recovered, containing a quantity of Zr equal to 2.91% which decreases to 2.75% after extraction in Soxhlet with toluene for 24 hours.

EXAMPLES 7–13

Polymerization 500 ml of toluene (previously distilled on metallic sodium) and a volume of solution at 10% in toluene of methylaluminoxane (MAO, WITCO commercial product) are charged into a 1 liter Buchi glass pressure-resistant reactor, equipped with a propeller stirrer, thermoresistance and heating jacket connected to a thermostat for the temperature control, maintained under vacuum for at least two hours interrupted by three washings with nitrogen, so as to obtain the desired final ratio Al/(Ti or Zr). The temperature is brought to 70° C. and the suspension of supported titanium or zirconium complex obtained by dispersing in toluene (15–20 ml) a quantity of catalyst (50–100 mg) which is such that the concentration of metal in the reactor is about 10$^{-5}$M, is introduced. The reactor is pressurized to the desired pressure (2–4 atm) with ethylene and the polymerization is carried out for 15–60 minutes. The polyethylene (PE) thus formed finally precipitates, by pouring the reaction mixture into 1 liter of methanol acidified with HCl and maintained under vigorous stirring. The polymer is then filtered, washed twice with acetone and left to dry in the air 24 hours.

Several polymerization tests were carried out with this procedure, corresponding to examples 7 to 13, using the complexes prepared as described in the previous examples. The specific polymerization conditions and results obtained are shown in table 1 below, in which each supported complex (column Comp.) is identified by reference to the preparation example.

TABLE 1

| Ex. | Comp. (Ex. Nr) | M/[M] (mmol $10^5$) | Al/M | P(atm)/ t(min) | Yield ($g_{PE}$) | Activity ($g_{PE}$/mmol M · hour · atm) |
|---|---|---|---|---|---|---|
| 7 | 1 | Zr/0.08 | 2500 | 4/60 | 0.2 | 128 |
| 8 | 2 | Ti/2.0 | 500 | 4/60 | 2.2 | 53 |
| 9 | 3 | Ti/0.2 | 2500 | 4/60 | 2.5 | 624 |
| 10 | 3 | Ti/2.0 | 500 | 4/60 | 2.9 | 72 |
| 11* | 4 | Ti/2.0 | 500 | 4/60 | 0.7 | 19 |
| 12 | 5 | Zr/5.3 | 200 | 2/15 | 13.3 | 629 |
| 13* | 6 | Zr/6.2 | 200 | 2/15 | 13.0 | 529 |

* = comparative

We claim:

1. A process for the preparation of a metallocene complex of titanium, zirconium or hafnium, supported on an inorganic solid, comprising the following steps in succession:
   (a) putting in contact and reacting an inorganic solid having hydroxide groups on the surface, which are reactive with an alkoxysilane group, with at least one organic compound having the following formula (II):

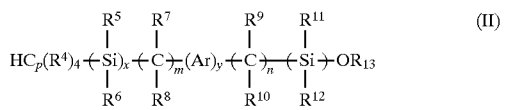

wherein:
   $C_p$ represents a cyclopentadienyl ring; each $R^4$ can independently be hydrogen, halogen, a $C_1$–$C_8$ alkyl group, a $C_3$–$C_{12}$ alkylsilyl group, a $C_5$–$C_8$ cycloalkyl group, a $C_6$–$C_{14}$ aryl group, a $C_6$–$C_{15}$ arylalkyl group, a $C_1$–$C_8$ alkoxy group, a $C_1$–$C_8$ alkylcarbonyloxy group, or two adjacent $R^4$ groups can combine with each other to form an aliphatic or aromatic cyclic structure comprising in the cycle at least three non-metal atoms different from hydrogen and halogen;
   $R^5$ and $R^6$ can, independently of each other, be a $C_1$–$C_5$ alkyl group, a $C_5$–$C_8$ cycloalkyl group, a $C_6$–$C_{12}$ aryl group, a $C_7$–$C_{12}$ arylalkyl group or a $C_1$–$C_5$ alkoxy group;
   $R^7$, $R^8$, $R^9$ and $R^{10}$ can, independently of each other, be hydrogen, a $C_1$–$C_5$ alkyl group, a $C_5$–$C_8$ cycloalkyl group, a $C_6$–$C_{12}$ aryl group, a $C_7$–$C_{12}$ arylalkyl group or a $C_1$–$C_5$ alkoxy group;
   $R^{11}$ and $R^{12}$ can, independently of each other, be a $C_1$–$C_5$ alkyl group, a $C_5$–$C_8$ cycloalkyl group, a $C_6$–$C_{12}$ aryl group, a $C_7$–$C_{12}$ arylalkyl group or a $C_1$–$C_5$ alkoxy group;
   $R^{13}$ is a $C_1$–$C_5$ alkyl group;
   Ar is a $C_3$–$C_{16}$ divalent aromatic or heteroaromatic group;
   the indexes "m" and "n" can be 0, or can independently have all the integer values between 1 and 4,
   the indexes "x" and "y" can independently have the value of 0 or 1,
   to obtain an inorganic solid functionalized with cyclopentadienyl groups;
   (b) putting in contact and reacting, in an inert liquid medium, said functionalized inorganic compound with a compound of a metal M having the following formula (III):

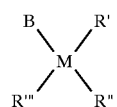

wherein:
   M represents a metal selected from titanium, zirconium or hafnium;
   R' and R" each independently represent a substituent group selected from a hydrogen or halogen atom, a $C_1$–$C_8$ alkyl group, a $C_3$–$C_{12}$ akylsilyl group, a $C_5$–$C_8$ cycloalkyl group, a $C_6$–$C_{10}$ aryl group, a $C_1$–$C_8$ alkoxy group, a $C_2$–$C_{10}$ dialkylamide group and a $C_4$–$C_{20}$ alkylsilylamide group;
   R''' represents a substituent group of the same nature as the previous groups R' and R", selected independently of these, or an anion containing an $\eta^5$-cyclopentadienyl ring co-ordinated to the metal M; and
   B represents a $C_1$–$C_8$ alkyl group, a $C_5$–$C_8$ cycloalkyl group, a $C_6$–$C_{10}$ aryl group or a $C_2$–$C_{10}$ dialkylamide group;
to form said supported metallocene complex.

2. The process according to claim 1, wherein, in said compound having formula (II), the groups $R^5$, $R^6$, $R^{11}$ and $R^{12}$ are methyl or ethyl, and the groups $R^7$, $R^8$, $R^9$ and $R^{10}$ are hydrogen, methyl or ethyl.

3. The process according to claim 1 or 2, wherein, in said compound having formula (II), the indexes "m", "x" and "y" are 0.

4. The process according to claim 3, wherein, in said compound having formula (II), the index "n" is 0.

5. The process according to claim 1, wherein the group "$HC_p(R^4)_4$", in said compound having formula (II), is a cyclopentadienyl, indenyl, 4,5,6,7-tetrahydroindenyl group or a (poly)methylsubstituted derivative of these.

6. The process according to claim 1, wherein said inorganic solid in step (a) is a porous oxide of a metal M' selected from silicon, aluminum, titanium, zinc or magnesium.

7. The process according to claim 6, wherein said porous oxide is granular silica, alumina or a silicoaluminate having an average particle size of between 5 and 200$\mu$, a pore volume of between 1 and 3 ml/g and an available surface of between 50 and 400 m$^2$/g, with a concentration of M'—OH groups on the surface of between 0.1 and 2.0 mmoles/g.

8. The process according to claim 1, wherein the group B in the compound having formula (III) is a dialkylamide group having the formula —$NR^{14}R^{15}$ wherein $R^{14}$ and $R^{15}$ are alkyl groups having from 1 to 4 carbon atoms.

9. The process according to claim 1, wherein at least two of the groups R', R" and R''' of the compound having formula (III) are $C_1$–$C_8$ alkyl, or dialkylamide having the formula —$NR^{14}R^{15}$ wherein $R^{14}$ and $R^{15}$ are alkyl groups having from 1 to 4 carbon atoms.

10. The process according to claim 1, wherein said groups R', R" and R''' and B, in the compound having formula (III), are equal to each other and are dimethylamide or diethylamide.

11. The process according to claim 1, wherein said groups R', R" and B, in the compound having formula (III), are equal to each other and are dimethylamide or diethylamide, and said group R''' is an $\eta^5$-cyclopentadienyl group co-ordinated to the metal M.

12. The process according to claim 1, wherein said step (a) is carried out by putting in contact and reacting the compound having formula (II) with said inorganic solid in an inert liquid medium, at a temperature of 50° to 300° C., for a time of 1 to 10 hours.

13. The process according to claim 12, wherein said step (a) is carried out at reflux of said inert liquid medium.

14. The process according to claim 1, wherein said step (b) is carried out in an inert liquid medium, 70° to 150° C., and for a period of 4 to 12 hours.

15. The process according to claim 12, wherein said temperature ranges from 180° to 250° C.

16. The process according to claim 14, wherein said temperature ranges from 90° to 130° C.

17. The process according to claim 14, wherein said inert liquid medium consists of an aromatic hydrocarbon solvent.

* * * * *